United States Patent [19]

Timberlake et al.

[11] Patent Number: 5,180,859

[45] Date of Patent: Jan. 19, 1993

[54] PROCESS FOR THE PRODUCTION AND RECOVERY OF HALONITROALKANES IN HIGH YIELD

[75] Inventors: Larry D. Timberlake, West Lafayette; James L. Brennan, Lafayette, both of Ind.

[73] Assignee: Great Lakes Chemical Corporation, West Lafayette, Ind.

[21] Appl. No.: 910,005

[22] Filed: Jul. 7, 1992

[51] Int. Cl.$^5$ .......................................... C07C 205/01
[52] U.S. Cl. .................................. 568/946; 568/958
[58] Field of Search .................. 568/946, 958; 208/68, 208/57

[56] References Cited

U.S. PATENT DOCUMENTS

| | | | |
|---|---|---|---|
| 2,632,776 | 3/1953 | Slagh | 260/644 |
| 4,922,030 | 5/1990 | Nocito et al. | 568/713 |
| 5,043,489 | 8/1991 | Nocito et al. | 568/946 |

*Primary Examiner*—James H. Reamer
*Attorney, Agent, or Firm*—Woodard, Emhardt, Naughton, Moriarty & McNett

[57] ABSTRACT

A process for the preparation of halonitroalkanes, e.g. bromonitromethane, is disclosed in which a nitroalkane is reacted with an alkali metal base or an alkaline earth metal base, and the resulting nitroalkane salt is halogenated to form the halonitroalkane in a reaction mixture. The process is improved by acidifying the reaction mixture, preferably to pH=0-4, and thereafter recovering the halonitroalkane by azeotropic distillation of the reaction mixture. The acidification step increases the amount of halonitroalkane recovered, as compared to prior art processes in which the reaction mixture is distilled without prior acidification.

12 Claims, No Drawings

PROCESS FOR THE PRODUCTION AND RECOVERY OF HALONITROALKANES IN HIGH YIELD

BACKGROUND OF THE INVENTION

1. Field of the Invention

The present invention relates to processes for the preparation of halonitroalkanes, e.g. bromonitromethane, and particularly to an improved method for the recovery of halonitroalkanes from a reaction mixture.

2. Description of the Prior Art

Processes for the production of halonitroalkanes such as bromonitromethane are well known in the art. The conventional method for preparing bromonitromethane is disclosed in U.S. Pat. No. 2,632,776, issued to Slagh on Mar. 24, 1953. This process comprises first reacting nitromethane with an alkali metal hydroxide, calcium hydroxide or barium hydroxide to yield the nitromethane salt in solution. Bromine is then admixed with the salt solution and the bromonitromethane readily forms and is recovered by steam distillation. This process is reported to be useful in preparing bromonitromethane in yields of 70–90% of theoretical.

Similar processes for the preparation of halonitroalkanes are described in U.S. Pat. Nos. 4,922,030 and 5,043,489, issued to Nocito et al. on May 1, 1990 and Aug. 27, 1991, respectively. The disclosures of the Slagh and Nocito et al. patents relating to the basic two-step process for preparing halonitroalkanes are hereby incorporated.

The prior art has recognized the need to control various parameters of the basic reaction scheme in order to obtain halonitroalkanes in high yield. The Slagh patent recognizes the importance of controlling a number of factors, including the proportions of nitroalkane, alkali, water and bromine used; the temperatures at which the salt formation and bromination are performed; the time between formation of the salt and its subsequent bromination; and the rate of addition of bromine. The Nocito et al. patents also emphasize many of the foregoing considerations, and also suggest the use after the second step of a compound, such as sodium bisulfite, to destroy unreacted bromine to avoid over bromination of the nitroalkane.

One method of recovery of the prepared halonitroalkane is by extraction, for example using methylene chloride (MDC). The MDC layer is isolated and the MDC is removed under reduced pressure at temperatures below about 30° C., and no product degradation occurs. However, this introduces a solvent into an otherwise organic solvent-free system, and adds additional costs to the process.

Alternatively, the halonitroalkane may be recovered by azeoptropic distillation, e.g. steam distillation. However, it has been determined that the recovery of halonitroalkanes by steam distillation of the reaction effluent results in loss of some of the product, resulting in reduced yield. There has therefore remained a need to provide for an improved recovery of the formed halonitroalkane in order to obtain increased overall yield from this conventional, two-step formation process.

SUMMARY OF THE INVENTION

Briefly describing one aspect of the present invention, there is provided an improved method for the production of halonitroalkanes. The halonitroalkane is prepared in conventional manner by the reaction of the corresponding nitroalkane with an alkali metal base or an alkaline earth metal base to form the nitroalkane salt, and thereafter brominating the salt to form a reaction mixture containing the halonitroalkane. The reaction mixture is then acidified to pH=0–4, preferably pH=1–3, and the acidified mixture is azeotropically distilled to yield the halonitroalkane.

It is an object of the present invention to provide a process for the production of halonitroalkanes, e.g. bromonitromethane, in high yield. A further object of the present invention is to provide an improved method for the recovery of halonitroalkanes from a reaction mixture by azeotropic distillation.

Further objects and advantages of the present invention will be apparent from the description of the preferred embodiment which follows.

DESCRIPTION OF THE PREFERRED EMBODIMENT

For the purposes of promoting an understanding of the principles of the invention, reference will now be made to the preferred embodiment thereof, and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

The present invention relates to an improved process for the preparation and recovery of halonitroalkanes, such as bromonitromethane. The basic, two-step preparation of these compounds is suitably demonstrated by the process for preparing bromonitromethane, which is conventional and well within the skill in the art. This basic process comprises the conversion of nitromethane to a salt, for example in accordance with the following reaction:

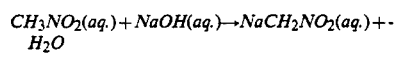

$$CH_3NO_2(aq.) + NaOH(aq.) \rightarrow NaCH_2NO_2(aq.) + H_2O$$

The nitromethane salt is then brominated, again in conventional fashion as exemplified by the following reaction:

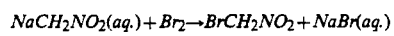

$$NaCH_2NO_2(aq.) + Br_2 \rightarrow BrCH_2NO_2 + NaBr(aq.)$$

The second reaction mixture is then azeotropically distilled to recover the bromonitromethane. In contrast to the prior art, however, in accordance with the present invention the reaction effluent is first acidified to reduce the pH, and the mixture is then distilled. The use of this acidification step reduces degradation of the halonitroalkane, and produces a higher yield of product than would otherwise result.

The process of the present invention has application to the preparation of monohalogenated nitroalkanes of the formula:

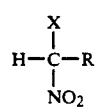

in which R is hydrogen or a lower alkyl group, e.g. a $C_1$–$C_4$ alkyl group, and X is a halogen. The reaction involves the reaction of a mono alkali salt of a nitroalkane, i.e., a nitronate salt, with a halogen to form the monohalogenated nitroalkane which is subsequently recovered from the reaction mixture.

Preparation of the nitronate salt is achieved by the straightforward addition of the nitroalkane and a suitable alkali metal base or alkaline earth metal base. Sodium hydroxide is preferred for this purpose, although various alkali metal bases or alkaline earth metal bases may be used, including for example potassium hydroxide, calcium hydroxide, barium hydroxide, and mixtures thereof. As is known in the art, essentially equal molar quantities, e.g. 0.8:1 to 1.1:1, of the alkali and nitroalkane are preferably used.

The reaction is conducted with agitation at a temperature between about $-10°$ C. and about 40° C., preferably between 0° C. and 30° C. This reaction is exothermic, and may occur in any suitable vessel equipped with an agitator and cooling jacket, preferably a continuous reactor consisting of a tube containing a static mixer. Typically, an aqueous solution of the nitroalkane is mixed with an aqueous solution of the base, resulting in an aqueous solution of the nitronate salt. However, other suitable solvents may be employed.

The resulting nitronate salt is brominated also in conventional fashion. For example, the nitronate salt may be admixed with bromine or a tribromide salt in a suitable reaction vessel, and the reaction proceeds with agitation. Since the bromination reaction is exothermic, cooling is applied to maintain the reduced temperatures as indicated previously.

In a continuous system, anhydrous bromine or a bromine solution, preferably aqueous, is fed into a tube reactor equipped with a static mixer simultaneously and in essentially equal molar quantity with the nitronate salt solution. Water is the preferred solvent, although other suitable solvents may be used when desired. Also, as noted in the Slagh patent, a soluble metal bromide salt, e.g. sodium bromide or potassium bromide, may be dissolved in the aqueous nitronate solution to increase the solubility of bromine in the solution, and thereby to facilitate distribution of bromine throughout the mixture.

An example of the foregoing two-step process is as follows. A 9% aqueous solution of nitromethane, precooled to 5° C., was pumped concurrently with a 5.291% aqueous solution of NaOH, also precooled to 5° C., into a ¼" I.D. static mixer, 17.3 feet long, immersed in a dry ice bath. The aqueous product, containing the sodium salt of nitromethane, was passed to a brominator. Bromine was introduced at the same end of the brominator as the sodium nitromethane. The overall length of the brominator was 24.5 inches, with the last 16.5 inches jacketed. The product effluent, a mixture of organic liquid and water, was drained into a receiver for workup. About half of the product resided in the aqueous phase. Both steps were very exothermic and required good cooling, as well as good turbulence for proper mixing.

The resulting halonitroalkane is recovered from the reaction mixture by azeotropic distillation, for example at a temperature of about 90°-100° C. The distillate forms a lower layer of the brominated nitroalkane product and an upper aqueous layer having a minor amount of the product dissolved therein. The lower layer of product is separated, for example by decantation from a suitable distillation trap. The upper layer may be advantageously redistilled to recover a further amount of the product.

In contrast to the prior art, it has been discovered that the pH of the aqueous halonitroalkane reaction mixture at the time of distillation is controlling of the amount, i.e. percentage, of product recovered. 1 or the standard two-step process as previously outlined, the pH of the final reaction mixture will fluctuate slightly, depending on the relative amounts of reactants used, but will generally fall in the range of pH=5-7. However, in accordance with the present invention the recovery of the halonitroalkane from the reaction mixture is significantly increased by first adjusting the pH of the mixture to pH=0-4, preferably pH=1-3, before conducting the azeotropic distillation.

Any mineral acid, such as sulfuric or hydrochloric acid, can be used for the acidification of the reaction mixture. In the case of preparing bromonitroalkanes such as bromonitromethane, hydrobromic acid is preferred since bromide ion is already present in the medium. Upon distillation of the reaction mixture having pH=0-4, preferably pH=1-3, the amount of halonitroalkane recovered is significantly higher than would have been recovered absent the prior acidification step.

It will further be appreciated that the present invention provides a method for improving various processes for the production of halonitroalkanes in which the halonitroalkane is recovered by azeotropic distillation from a reaction mixture. As demonstrated hereafter, it has been discovered that the amount of halonitroalkane lost during the distillation recovery is dependent on the pH of the mixture prior to distillation, the losses increasing with higher pH. Thus, improved recovery is accomplished by the step of reducing the pH of the reaction mixture prior to distillation, especially where the pH of the reaction mixture, prior to pH adjustment, is at least about 5. Preferably, the pH is reduced by at least about 1, and preferably the pH is reduced as previously indicated to the range of pH=0-4, most preferably pH=1-3.

EXAMPLE 1

The 2-step continuous synthesis of bromonitromethane without the acidification step was performed as follows. An aqueous solution of nitromethane (NM) was fed into a tubular reactor fitted with static mixers and external cooling capability. Simultaneously, an aqueous sodium hydroxide solution was fed into the same reactor, thus forming the sodium salt of nitromethane. The effluent from this first reactor was fed into a second tubular reactor where aqueous sodium tribromide was introduced. Bromine can also be used as the brominating agent. The reaction stoichiometry was maintained at 1.00:0.90:0.92 NM:NaOH:$Br_2$ by the use of controlled metering pumps.

The reaction effluent pH was 5.7 and contained a product oil layer and an aqueous phase which also contained product. The mixture was azeotropically distilled using a Dean-Stark trap and the product layer was drawn off semi-continuously in the distillate. The final product assay was 91.4% bromonitromethane.

EXAMPLE 2

This example compares the assay of azeotropically distilled BNM vs. the undistilled BNM oil layer, both without an acidification step. The amount of degradation of BNM as a function of pH is demonstrated. The process of Example 1 was performed several times on pilot plant scale. The average results from each continuous run are indicated in Table I. It is apparent that distillation of the non-acidified reaction mixture results in a significant loss of BNM in the recovery process.

TABLE I

| Run No. | Oil layer wt % BNM | Distilled wt % BNM | % BNM Degraded | Effluent pH |
|---|---|---|---|---|
| 1 | 94.7 | 85.7 | 9.5 | 6.4 |
| 2 | 94.8 | 88.1 | 7.1 | 6.0 |
| 3 | 95.6 | 91.4 | 4.4 | 5.7 |

EXAMPLE 3

This example compares assays obtained both with and without the acidification step. Effluent samples were taken from the run nos. 2 and 3 of Example 2. These samples were azeotropically distilled in the lab with and without adjusting the pH using 48% aq. HBr. Additionally, the reaction aqueous phase was extracted without pH adjustment using methylene chloride (MDC) and the MDC was removed under vacuum below 30° C. The results are shown in Table II.

TABLE II

| Run No. | Sample Type | pH | GC wt % BNM |
|---|---|---|---|
| 2 | Oil layer | — | 93.3 |
|   | Aq. layer* | — | 93.6 |
|   | Distilled | 6.0 | 88.5 |
| 3 | Oil layer | — | 94.9 |
|   | Aq. layer* | — | 95.0 |
|   | Distilled | 6.1 | 89.1 |
| 3 | Oil layer | — | 94.9 |
|   | Aq. layer* | — | 94.6 |
|   | Distilled adjusted w/ 48% HBr | 3.0 | 93.5 |

*MDC extraction

EXAMPLE 4

The same procedure was used as in Example 1, but the product was acidified from pH 5.9 to 3.0 using 48% aq HBr before azeotropic distillation. The reaction oil layer before distillation was 93.5% BNM. By comparison, the distilled product assay was 93.2% BNM.

EXAMPLE 5

Repetition of the procedure of Example 4 is performed, with the reaction effluent prior to distillation being adjusted to a pH of 0-4, including particularly pH=2-3. Increased yield of bromonitromethane is achieved. Similarly advantageous results are achieved upon repeating the foregoing examples for the preparation of other halonitroalkanes, for example those in which the halo component is chloro, fluoro or iodo, and those for which the alkane is ethane, propane, etc. Similarly, repetition of the foregoing examples using other alkali metal bases and alkaline earth metal bases results in increased yield over the same processes performed without acidification prior to distillation.

While the invention has been described in detail in the foregoing description, the same is to be considered as illustrative and not restrictive in character, it being understood that only the preferred embodiment has been shown and described and that all changes and modifications that come within the spirit of the invention are desired to be protected.

What is claimed is:

1. In a method for the production and recovery of a halonitroalkane, the method including the preparation of the halonitroalkane in a reaction mixture at a final pH of at least about 5.0, the method further including the recovery of the halonitroalkane from the reaction mixture by azeotropic distillation, the improvement comprising:

adjusting the pH of the reaction mixture to pH=0-4 prior to distillation recovery of the halonitroalkane, and thereafter recovering the halonitroalkane by azeotropic distillation.

2. The improvement of claim 1 in which said adjusting is to a pH of 1-3.

3. The improvement of claim 1 in which the halonitroalkane is bromonitromethane.

4. The improvement of claim 3 in which said adjusting is to a pH of 1-3.

5. A process for the preparation of a halonitroalkane which comprises the steps of:

a. reacting a nitroalkane with an alkali metal base or an alkaline earth metal base to form the nitroalkane salt;

b. halogenating the nitroalkane salt produced by step a. to yield a reaction mixture including the halonitroalkane and having a pH of at least about 5;

c. reducing the pH of the reaction mixture of step b. to pH=0-4; and d. after step c., recovering the halonitroalkane by azeotropic distillation of the pH-adjusted reaction mixture.

6. The process of claim 5 in which step c. comprises adjusting the pH to pH=1-3.

7. The process of claim 5 in which step a. comprises reacting an aqueous solution of the nitroalkane with an aqueous solution of the alkali metal base or alkaline earth metal base.

8. The process of claim 5 in which said reacting of step a. is at a temperature of between about −10° C. and about 40° C.

9. The process of claim 5 in which said halogenating of step b. is at a temperature of between about −10° C. and about 40° C.

10. The process of claim 5 in which step a. comprises reacting a nitromethane to form the nitromethane salt.

11. The process of claim 10 in which step b. comprises brominating the nitromethane salt.

12. A process for the preparation of a halonitroalkane which comprises the steps of:

a. reacting a nitroalkane with an alkali metal base or an alkaline earth metal base to form the nitroalkane salt;

b. halogenating the nitroalkane salt produced by step a. to yield a reaction mixture including the halonitroalkane;

c. reducing the pH of the reaction mixture of step b. by at least about 1; and d. after step c., recovering the halonitroalkane by azeotropic distillation of the pH-adjusted reaction mixture.

* * * * *